(12) United States Patent
Moore

(10) Patent No.: US 6,387,412 B1
(45) Date of Patent: May 14, 2002

(54) STORAGE STABLE ANIMAL MINERAL GRANULES

(75) Inventor: William P. Moore, Hopewell, VA (US)

(73) Assignee: Agri-Nutrients Technology Group, Inc., Disputanta, VA (US)

( * ) Notice: Subject to any disclaimer, the term of this patent is extended or adjusted under 35 U.S.C. 154(b) by 0 days.

(21) Appl. No.: 09/550,234

(22) Filed: Apr. 14, 2000

(51) Int. Cl.⁷ .............. A61K 9/00; A61K 9/14; A61K 33/00; A61K 33/24; A61K 33/26; A61K 33/30; A61K 33/32; A23L 1/304; A23L 1/175

(52) U.S. Cl. .............. 424/490; 424/400; 424/438; 424/442; 424/489; 424/630; 424/639; 424/641; 424/646; 424/657; 424/661; 424/667; 424/677; 424/678; 424/679; 424/680; 424/681; 424/682; 424/702; 424/703; 514/52; 514/54; 514/64; 514/167; 514/168; 514/251; 514/276; 514/355; 514/563; 514/458; 514/492; 514/494; 514/499; 514/500; 514/501; 514/502; 514/706; 514/725; 514/769; 514/904; 514/905; 514/951; 426/72; 426/73; 426/74; 426/648; 426/805; 426/806; 426/807

(58) Field of Search .............. 424/438, 489, 424/490, 400, 442, 630, 639, 641, 646, 657, 661, 667, 677, 678, 679, 680, 681, 682, 702, 703; 426/72, 73, 74, 648, 805, 806, 807; 514/52, 54, 64, 167, 168, 251, 276, 355, 563, 458, 492, 494, 499, 500, 501, 502, 706, 725, 769, 904, 905, 951

(56) References Cited

U.S. PATENT DOCUMENTS 5,019,148 A * 5/1991 Moore ............................ 71/11
5,273,547 A * 12/1993 Reidies ......................... 8/107

FOREIGN PATENT DOCUMENTS

| EP | 357327 | * | 3/1990 |
| GB | 2123693 | * | 2/1984 |
| WO | 01/22943 | * | 4/2001 |

\* cited by examiner

Primary Examiner—John Pak

(57) ABSTRACT

A storage stable magnesium oxychloride coated granular animal feed mineral supplement composition resistant to disintegration cause by moisture absorption and attrition, comprising granular mineral nutrients useful as animal feed supplements and magnesium oxychloride coatings amounting to between 0.5 and 10.0 percent of the weight of the granules, formed on the granules of mineral nutrients by coreaction of magnesium chloride and magnesium oxide. An additional coating of between 0.2 and 2.0 percent magnesium stearate formed on the magnesium oxychloride may be used to decrease the rate of wetting of the granular animal feed mineral supplements.

11 Claims, No Drawings

STORAGE STABLE ANIMAL MINERAL GRANULES

FIELD OF THE INVENTION

This invention concerns animal feed minerals and more particularly a new coated granular mineral supplement composition which is storage stable in the high moisture-high attrition conditions which mineral feed supplement products are usually subjected to in practical commercial usage. The magnesium oxychloride coated granules are resistant to disintegration from wetting and drying cycles and mechanical abuse during shipping, handling, storage, and blending.

BACKGROUND OF THE INVENTION

For satisfactory animal health, particularly in the production of commercial animals the use of mineral feed supplements in the feed rations of the animals is essential. These minerals normally are stored in places such as open bins, piles on the floors of open buildings, and even out of doors in the weather. They are subjected to mechanical abrasion by devices such as paddle mixers, paddle and screw conveyors, and dumping from one container to another. The handling of animal mineral supplement products is particularly demanding in the large scale production of commercial beef, dairy, and swine animals.

The mineral feed supplements are normally produced as concentrated mixtures by blending together mineral compounds such as dicalcium phosphate, magnesium sulfate, ferrous sulfate, manganous sulfate, zinc sulfate, cobalt sulfate, copper sulfate, calcium iodate, potassium chloride, sodium chloride, and selenium concentrate. These mixtures when dry tend to segregate and become unpalatable and unacceptable to the feeding animals.

These mineral mixtures absorb and desorb moisture when stored in practical areas of use. As they absorb moisture they form large clumps and lumps which do not break up even when they are dried again under conditions of low moisture and high heat which occur in a pasture, range, or feed lot. The clumps and lumps get harder as they age, even if dried, resulting in reduced consumption of these essential minerals.

An improvement in the physical and chemical integrity of animal mineral granules was provided by my U. S. Pat. No. 5,019,148 entitled "Homogeneous Mineral Granules By Acid-Base Reaction." In the method commodity metal oxides were reacted with acids, such as phosphoric acid, to form homogeneous mineral particles which largely eliminated the problem of segregation of a mineral mixture.

Unfortunately, the improved mineral product was not as storage stable as needed under practical operating conditions, particularly where the mineral granules were subjected to moist air, rain, or high attrition storage, handling, and distribution.

OBJECTS OF THE INVENTION

It is therefore an object of this invention to provide a particulate animal feed mineral supplement composition which is storage stable under conditions of commercial use.

It is another object of this invention to provide a storage stable particulate animal feed mineral supplement composition which is resistant to moisture and attrition.

It is another object of this invention to provide a granular animal feed mineral composition which is resistant to disintegration caused by moisture absorption and physical attrition.

SUMMARY OF THE INVENTION

I have now discovered that when a coating of magnesium oxychloride is formed by the coreaction of magnesium chloride and magnesium oxide on particles of animal minerals, a storage stable particulate animal mineral composition is formed which exhibits improved resistance to attrition and moisture and which does not form palatability destroying hard clumps and lumps when subjected to wetting and drying. The new composition may effectively be coated with another coating, magnesium stearate to decrease moisture penetration into the feed mineral particles if desired. Salt and vitamins may also be included as part of the new composition.

DISCUSSION OF THE INVENTION

A storage stable magnesium oxychloride coated particulate animal feed mineral supplement composition has been discovered which comprises particles of mineral materials useful as animal feed supplements and exhibit diameters between 0.7 and 4.0 millimeters. Particles smaller than about 0.7 millimeters in diameter are difficult to coat without the use of undesirably large amounts of magnesium oxychloride coating and particles larger than 4.0 millimeters in diameter while readily coatable are too large to be palatable in the feed rations of most animals.

Magnesium oxychloride coatings amounting to between 0.5 and 10.0 percent of the weight of the particles, formed on the particles of mineral nutrients by coreaction of magnesium chloride and magnesium oxide, form an effective composition. The use of less than 0.5 percent magnesium oxychloride coating provides less than the required amount of wet strength and resistance to attrition. Although more than 10 percent magnesium oxychloride provides desirable physical properties and strength, it reduces palatability of the mineral supplement granule.

The magnesium oxychloride coating is most effectively formed by coreacting magnesium chloride in aqueous solution and magnesium oxide powder on the particles of mineral nutrients. The magnesium chloride solution used is preferably a strong one exhibiting concentrations between 50 and 60 percent by weight. The magnesium oxide powder may be any one of the commercially available products, preferably with 70 percent, or more, of the particles fine enough to pass through a 300 mesh U.S. Standard Screen. The magnesium oxychloride coating may be formed on the mineral supplement particles in a single reaction but is preferably formed in a plurality of layered reactions wherein small amounts of magnesium chloride additions are followed by intermittent small additions of magnesium oxide.

Magnesium oxychloride is normally considered to be a chemical compound combining magnesium chloride and magnesium oxide in a one-to-one molecular ratio, and this combination provides an effective coating in the instant composition. However, the composition is effective where the magnesium oxychloride coating is formed by coreacting between 0.5 and 1.0 molecules of magnesium chloride per molecule of magnesium oxide. Outside of these ratios the coatings do not provide sufficient strength and water resistance.

A wide variety of mineral nutrients may be used in the new coated particulate animal feed mineral supplement composition. Normal mineral nutrients which are effective in the instant composition comprise chemical compounds containing metals essential to animal health including calcium, magnesium, iron, manganese, zinc, copper, and cobalt.

These normal mineral nutrients which are effective in the instant composition also comprise chemical compounds containing non metals essential to animal health including chlorine, iodine, sulfur, molybdenum, selenium, and boron.

It is usual that animal mineral nutrient supplements contain alkali metal chlorides. These alkali metal chlorides are effectively included in the instant storage stable magnesium oxychloride coated particulate animal feed in amounts between 1 and 15 percent by weight. The instant composition preferably contains between 5 and 15 percent by weight sodium chloride and between 0.1 and 1.0 percent potassium chloride.

The palatability of the composition is enhanced where the particulate mineral nutrients contain cane molasses amounting to between 1 and 3 weight percent on a dry basis. The molasses may be supplied to the composition in the liquid or dry form. Optimum palatability is not achieved until a concentration of 1 percent molasses is reached. The particles of the composition are undesirably sticky when molasses concentrations higher than 3 percent are included in the composition.

The preferred storage stable magnesium oxychloride coated particulate animal feed mineral supplement composition contains vitamins essential to animal health including the especially important vitamins A, B, D, and E. Although the composition is effective without the vitamins it is desirable that the vitamins be included in the composition, and the vitamins may be effectively included as a mixture in the composition in amounts between 0.05 and 0.30 percent by weight without detracting from its physical properties.

Resistance of granular animal feed mineral supplements to moisture is very important in their practical use. It is not necessary that these granules not absorb moisture or water. It is most necessary that the granules do not disintegrate so that they will not be consumed by the animals. In practical use the wet granules also dry after the source of humidity is removed. When wet and disintegrated granules dry, they form clumps, lumps and crusts. It is important that these events do not occur. Therefore, it is important that the animal feed mineral supplement granules retain their wet strength, do not disintegrate under moist conditions, do not form wet lumps and clumps, and do not form hard crusts when dry after being wet.

It is also important that these particles be initially strong and resistant to attrition as initially produced and delivered in a practical commercial manner for use, and also after going through wet and dry cycles. When the particles may be wet and dried and retain their integrity and strength and be handled, stored, and applied without loss of resistance to attrition, they may be considered storage stable for all practical purposes.

Where it is desirable to reduce moisture absorption by the animal feed mineral supplement particles, a particularly effective particulate storage stable animal feed mineral composition which is resistant to moisture and attrition may be used. This composition comprises particles of mineral nutrients useful as animal feed supplements exhibiting diameters between 0.7 and 4.0 millimeters. These particles are coated with magnesium oxychloride coatings amounting to between 0.5 and 10.0 percent of the weight of the particles, formed on the particles of the mineral nutrients by coreaction of magnesium chloride and magnesium oxide. The magnesium oxychloride coated particles are coated with wetting resistant coatings of magnesium stearate amounting to between 0.2 and 2.0 percent of the weight of the particles, formed on top of the magnesium oxychloride coatings by coreaction of about two parts by weight of stearic acid with one part magnesium oxide. The final magnesium stearate coating does not make the granule totally free of water penetration, but the above small amounts significantly reduces the rate of moisture absorption by the feed mineral particles.

A preferred magnesium oxychloride coated granular animal feed mineral supplement composition which is resistant to disintegration caused by moisture absorption and physical attrition containing vitamins essential to animal health was discovered. It comprises granular mineral nutrients exhibiting diameters between 1.0 and 3.0 millimeters, comprising chemical compounds containing metals including calcium, magnesium, iron, manganese, zinc, copper, and cobalt. The composition also contains cane molasses amounting to between 1 and 2 percent on a dry weight basis, and a mixture of vitamins A, D, and E amounting to between 0.12 and 0.20 percent. The composition also contains magnesium oxychloride coatings amounting to between 2.0 and 4.0 percent of the weight of the particles, formed on the granular mineral nutrients by coreaction of between 0.5 and 0.9 molecules of magnesium chloride in aqueous solution per molecule of magnesium oxide.

The mineral nutrients in the foregoing preferred composition comprise chemical compounds containing one or more non metals including chlorine, iodine, sulfur, molybdenum, selenium, and boron. The mineral nutrients in the foregoing preferred composition may effectively contain between 5 and 15 percent by weight sodium chloride and between 0.1 and 1.0 percent potassium chloride.

The term percent used herein means percentage by weight unless specifically stated otherwise.

PREFERRED EMBODIMENT OF THE INVENTION

Having described the basic concept of the instant invention reference is now made to the following examples which are provided to illustrate the preferred compositions of the instant invention, the method of its preparation, and the effectiveness of the new composition.

EXAMPLE 1

This example illustrates the preparation and the physical and chemical characteristics of a preferred composition of the instant invention.

Particles of mineral nutrients useful as animal feed supplements exhibiting diameters between 0.7 and 4.0 millimeters were prepared by premixing the materials listed as follows:

| Materials | Pounds |
| --- | --- |
| Hydrated Lime, 51 Ca, 96 DM | 21.1100 |
| Gypsum 22 Ca, 17 (S), 90 DM | 3.6300 |
| Potassium Chloride, 51K, 99 DM | 0.3200 |
| Manganous Oxide, 62 Mn | 1.1000 |
| Zinc Oxide, 72 Zn | 1.3100 |
| Cooper Sulfate, 25 Cu, 17 (S), 98 DM | 0.6400 |
| Ferrous Sulfate, 30 Fe, 17 (S), 96 DM | 0.0400 |
| Sodium Chloride, 60.7 Cl, 39.3 Na, 98.5 DM | 10.5600 |
| Calcium Iodate, 63.5 I | 0.0290 |
| Cobalt Carbonate, 49 Co | 0.0075 |
| Selenium Concentrate, 1 Se | 0.0990 |
| Bentonite | 3.8100 |

The premixed dry powders were charged at ambient temperature to an Eirich R-08 reactor-granulator, equipped with a rotor which operated in the opposite direction to the pan which rotated at an angle of 15 degrees from horizontal. The water and phosphoric acid were preheated to 190OF and added at an even rate throughout a three minute period, exothermically reacting with the metal oxides. One minute after the acid addition was completed much of the moisture in the mixture was evaporated and damp granules formed.

A commercial mixture of vitamins A, D, and E weighing 0.16 pounds was premixed with 3.19 pounds of cane molasses (60 percent solids) and was charged to the mixture while the Eirich was still operating and cooling quickly. The mixing-granulation was allowed to continue for an additional 30 seconds. The granules were discharged from the Eirich reactor-granulator and drying of the granules was completed in a rotary dryer by a air-combustion gas mixture. The granules were then screened to obtain granules exhibiting diameters between 0.7 and 4.0 millimeters. The undersize and oversize, after grinding, particles were used as recycle in subsequent preparations.

Granules exhibiting diameters between 0.7 and 4.0 millimeters amounting to 80 pounds were charged to the rotating pan of the Eirich R-08 machine with the rotor not operating. Magnesium oxychloride coatings were formed on the granules of mineral nutrients by coreaction of magnesium chloride and magnesium oxide. The materials were alternately added in two equal doses with the aqueous magnesium chloride added first. The total amounts of materials added are listed as follows:

| Materials | Pounds |
|---|---|
| Magnesium Chloride Solution, 11 Mg, 32 Cl | 10.5600 |
| Magnesium Oxide, 57 M9 | 2.0400 |

The reaction product is dried to provide a dry weight of magnesium oxychloride on the surface amounting to 7.6 percent of the granules. The composition was analyzed for the important mineral components and the results are listed as follows:

| Components | Wt % |
|---|---|
| Calcium | 16.72 |
| Phosphorous | 15.28 |
| Magnesium | 2.75 |
| Potassium | 0.35 |
| Chloride | 10.72 |
| Sodium | 6.11 |
| Sulfur | 1.60 |
| Cobalt | 0.005 |
| Iodine | 0.027 |
| Iron | 0.65 |
| Zinc | 1.40 |
| Selenium | 0.001 |
| Copper | 0.238 |
| Manganese | 0.98 |

EXAMPLE 2

This example demonstrates an effective composition of this invention, coated with magnesium stearate to reduce the rate of moisture absorption by the animal feed mineral supplement granules.

Product from Example 1, amounting to 50 pounds, was placed in a rotary drum dryer and was heated to 192° F. Then 0.41 pounds of commercial grade stearic acid and 0.205 pounds of magnesium oxide powder (93% passing through a 300 mesh U.S. Standard Screen) were added. The stearic acid melted, flowed onto the granules of magnesium oxychloride coated mineral supplement granules and reacted with the magnesium oxide to form a dry, solid magnesium stearate coating on the outside of the granules. The magnesium stearate coating amounted to 1.22% of the total weight of the granules.

EXAMPLE 3

This example is provided to illustrate the effectiveness, storage stability, granule strength and resistance to damage from wetting and drying of the products of the instant invention.

The product granules from Examples 1 and 2 were sampled and put through the physical tests exhibited in the following tables:

TABLE 1

Effect of Coating on Resistance to Attrition

| Granules Tested | Example 1 without coating | Example 1 with magnesium oxychloride coating | Example 2 coated with magnesium oxychloride plus magnesium stearate |
|---|---|---|---|
| Dry Crush Strength, lbs/granule | 1.86 | 2.45 | 2.03 |

The rates of dissolution of mineral from the granules were measured by submerging samples of the granules in water for two days and decanting the water.

The results of the tests are tabulated as follows:

TABLE 2

Effect of Coating on Condition of Granules After Wetting and Drying

| Granules Tested | Condition of the Granules after Soaking for 2 Days with Water and Drying to about 2.5 percent Moisture |
|---|---|
| Example 1, without coating | Granules largely disintegrated into fine particles when wet, and formed large hard agglomerated pieces with hard crusts when dried. |
| Example 1, with magnesium oxychloride coating | Granules intact with slight tendency to clump when wet, and granules remained n original form with no hard crusts when dried. |
| Example 2, with magnesium stearate covering the magnesium oxychloride coating | Granules intact with slight tendency to clump when wet, and granules remained in original form with no hard crusts when dried. |

TABLE 3

Effect of Coating on Moisture Absorption After Wetting and Drying

| Granules Tested | Increase in Weight of Granules After | | | | After 2 Days at ambient drying temperature |
|---|---|---|---|---|---|
| | 2 Days | 3 Days | 4 Days | 5 Days | |
| Example 1, without coating | 11.78 | 19.80 | 19.86 | 33.97 | 2.45 |
| Example 2, with magnesium oxychloride coating | 9.72 | 16.67 | 16.67 | 27.14 | 2.15 |
| Example 3, with magnesium stearate covering the magnesium oxychloride coating | 8.72 | 13.89 | 15.22 | 26.53 | 1.43 |

I claim:

1. A storage stable magnesium oxychloride coated particulate animal feed mineral supplement composition comprising:
   (a) particles of mineral nutrients useful as animal feed supplements exhibiting diameters between 0.7 and 4.0 millimeters; and,
   (b) magnesium oxychloride coatings amounting to between 0.5 and 10.0 percent of the weight of the particles, formed on the particles of mineral nutrients by coreaction of between 0.5 and 1.0 molecule of magnesium chloride per molecule of magnesium oxide.

2. The composition of claim 1 wherein the magnesium chloride is in aqueous solution and the magnesium oxide is in powder form.

3. The composition of claim 1 wherein the mineral nutrients comprise chemical compounds containing metals essential to animal health selected from the group consisting of calcium, magnesium, iron, manganese, zinc, copper, and cobalt.

4. The composition of claim 1 wherein the mineral nutrients comprise chemical compounds containing non metals essential to animal health selected from the group consisting of chlorine, iodine, sulfur, molybdenum, selenium, and boron.

5. The composition of claim 1 wherein the mineral nutrients contain alkali metal chlorides amounting to between 1 and 15 percent by weight.

6. The composition of claim 1 wherein the particulate mineral nutrients contain cane molasses amounting to between 1 and 3 weight percent on a dry weight basis.

7. The composition of claim 1 wherein the storage stable magnesium oxychloride coated particulate animal feed supplement contains vitamins essential to animal health selected from the group consisting of vitamins A, B, D, and E, amounting to a total of between 0.05 and 0.30 percent by weight.

8. A particulate storage stable animal feed mineral supplement composition resistant to moisture and attrition comprising:
   (a) particles of mineral nutrients useful as animal feed supplements exhibiting diameters between 0.7 and 4.0 millimeters;
   (b) magnesium oxychloride coatings amounting to between 0.5 and 10.0 percent of the weight of the particles, formed on the particles of mineral nutrients by coreaction of between 0.5 and 1.0 molecule of magnesium chloride per molecule of magnesium oxide; and,
   (c) wetting resistant coatings of magnesium stearate amounting to between 0.2 and 2.0 percent of the weight of the particles, formed on the magnesium oxychloride coating by coreaction of about two parts by weight stearic acid with one part by weight magnesium oxide.

9. A magnesium oxychloride coated granular animal feed mineral supplement composition resistant to disintegration caused by moisture absorption, and physical attrition, comprising:
   (a) granular mineral nutrients, exhibiting diameters between 1.0 and 3.0 millimeters, comprising (i) chemical compounds containing metals selected from the group consisting of calcium, magnesium, iron, manganese, zinc, copper, and cobalt, (ii) cane molasses, amounting to between 1 and 2 percent on a dry weight basis, and (iii) vitamins A, D, and E amounting to between 0.12 and 0.20 percent by weight; and
   (b) magnesium oxychloride coatings amounting to between 2.0 and 4.0 percent of the weight of the granules, formed on the granular mineral nutrients by coreaction of between 0.5 and 0.9 molecule of magnesium chloride in aqueous solution per molecule of magnesium oxide.

10. The composition of claim 9 wherein the mineral nutrients further comprise chemical compounds containing non metals selected from the group consisting of chlorine, iodine, sulfur, molybdenum, selenium, and boron.

11. The composition of claim 9 wherein the mineral nutrients further comprise between 5 and 15 percent by weight sodium chloride and between 0.1 and 1.0 percent potassium chloride.

* * * * *